United States Patent
Sellappan et al.

(10) Patent No.: US 9,932,620 B2
(45) Date of Patent: Apr. 3, 2018

(54) METHODS, DEVICES, AND SYSTEMS OF DETECTING MICROORGANISMS

(75) Inventors: Subramani Sellappan, Aurora, IL (US); Andrew Hearn, Chicago, IL (US); Salvatore Seminara, Chicago, IL (US)

(73) Assignee: CELSIS LTD., Westminster, London (GB)

( * ) Notice: Subject to any disclaimer, the term of this patent is extended or adjusted under 35 U.S.C. 154(b) by 932 days.

(21) Appl. No.: 13/537,267

(22) Filed: Jun. 29, 2012

(65) Prior Publication Data
US 2012/0301907 A1 Nov. 29, 2012

Related U.S. Application Data

(60) Provisional application No. 61/649,826, filed on May 21, 2012.

(51) Int. Cl.
| | | |
|---|---|---|
| *C12M 1/34* | (2006.01) | |
| *G01N 21/76* | (2006.01) | |
| *G01N 1/34* | (2006.01) | |
| *C12Q 1/04* | (2006.01) | |
| *G01N 21/77* | (2006.01) | |
| *G01N 1/38* | (2006.01) | |
| *G01N 33/569* | (2006.01) | |
| *G01N 1/02* | (2006.01) | |
| *G01N 1/40* | (2006.01) | |

(52) U.S. Cl.
CPC ............... *C12Q 1/04* (2013.01); *G01N 1/38* (2013.01); *G01N 21/76* (2013.01); *G01N 21/77* (2013.01); *G01N 33/56911* (2013.01); *G01N 2001/028* (2013.01); *G01N 2001/4061* (2013.01); *G01N 2001/4088* (2013.01); *G01N 2201/02* (2013.01)

(58) Field of Classification Search
None
See application file for complete search history.

(56) References Cited

U.S. PATENT DOCUMENTS

| | | | |
|---|---|---|---|
| 4,144,134 | A | 3/1979 | Plakas |
| 5,587,286 | A | 12/1996 | Pahuski et al. |
| 5,624,810 | A | 4/1997 | Miller et al. |
| 5,648,232 | A * | 7/1997 | Squirrell ................. 435/34 |
| 5,700,645 | A | 12/1997 | Pahuski et al. |
| 6,183,978 | B1 | 2/2001 | Bronstein et al. |
| 6,703,211 | B1 | 3/2004 | Schultz et al. |
| 2005/0026171 | A1 | 2/2005 | Hawkins et al. |
| 2007/0161085 | A1 | 7/2007 | Trager et al. |
| 2009/0203017 | A1 | 8/2009 | Dawson et al. |
| 2009/0269788 | A1 | 10/2009 | Patel |
| 2010/0209961 | A1 | 8/2010 | Kshirsagar et al. |
| 2011/0033924 | A1 | 2/2011 | Berry et al. |
| 2011/0143334 | A1 * | 6/2011 | Roscoe et al. ............. 435/5 |
| 2011/0197685 | A1 | 8/2011 | Alburty et al. |
| 2011/0314900 | A1 | 12/2011 | Blacklin et al. |

FOREIGN PATENT DOCUMENTS

| | | |
|---|---|---|
| WO | WO9417202 | 8/1994 |
| WO | WO9602666 | 2/1996 |
| WO | 2012031156 A1 | 3/2012 |

OTHER PUBLICATIONS

Banada et al. "Highly sensitive detection of *Staphylococcus aureus* directly from patient blood," Plos one 7,pp. 1-7, 2012.*
Aflalo C et al. "Continuous monitoring of adenosine 5'triphosphate in the microenvironment of immobilized enzymes by firefly luciferase." *Biochemistry*. Jun. 30, 1987; 26(13):3913-20.
Chen Y et al. "Detection of low-level microorganism by concomitant use of ATP amplification and bioluminescence assay". *Wei Sheng Wu Xue Bao*. Jun. 2009; 49(6):826-30. (English translated Abstract only).
Corbitt AJ et al. "Adenylate kinase amplification of ATP bioluminescence for hygiene monitoring in the food and beverage industry." *Letters in Applied Microbiology*. 2000; 30:443-447.
Guzmán Luna C et al. "Detection of somatic coliphages through a bioluminescence assay measuring phage mediated release of adenylate kinase and adenosine 5'-triphosphate." *J Virol Methods*. Oct. 2009;161(1):107-13. Epub Jun. 6, 2009.
Satoh T et al. "ATP Amplification for ultrasensitive bioluminescence assay: detection of a single bacterial cell." *Biosci. Biotechnol. Biochem*. Jun. 2004; 68(6):1216-20.
3M Microbiology. "Food Safety Maximized." Food Safety Products and Services Full Line. 2008.
PCT Search Report related to Application No. PCT/US2013/042114, dated Oct. 24, 2013.
PCT Search Report related to Application No. PCT/US2013/042116, dated Oct. 24, 2013.

* cited by examiner

*Primary Examiner* — David W Berke-Schlessel
(74) *Attorney, Agent, or Firm* — Loeb & Loeb LLP

(57) ABSTRACT

A rapid, sensitive method of separating and detecting microorganisms from a sample potentially containing microorganisms, such as but not limited to bacteria, fungi, yeast, viruses, and the like. The method relies on separation techniques to separate and concentrate the cells from the sample, together with chemical techniques to amplify the amount of detectable signal from low numbers of cells to provide a rapid and sensitive method of detecting microorganisms. This detection method may utilize: a filtration device; a centrifugation device; a system; a swab device; and kit comprising one or more of the devices and components to perform the present method of separating and detecting microorganisms in a sample potentially containing microorganisms. The sample may be a chemical, cosmetic, personal care, pharmaceutical, or consumable good in its raw material, in-process, and/or finished product states that needs to be tested for any contaminating microorganisms prior to shipment to the consumer.

7 Claims, No Drawings

METHODS, DEVICES, AND SYSTEMS OF DETECTING MICROORGANISMS

This application claims the benefit of U.S. Provisional Application No. 61/649,826, filed May 21, 2012 under 35 U.S.C. § 119(e), the content of which is hereby incorporated into this application by reference.

TECHNICAL FIELD

The innovative methods, devices, and systems relate to separating and detecting contaminating microorganisms from a sample, such as, food, chemical, cosmetic, pharmaceutical, and consumable goods in their raw material, in-process, and/or finished product states.

BACKGROUND

Chemical, cosmetic, personal care, pharmaceutical, and consumable products must be safe for consumers and some must comply with government regulations. Therefore, manufacturers of these products must test the products for any contamination with incoming raw materials during the manufacturing process and prior to shipping the finished products to wholesale and/or retail and pharmacy outlets for sale. While testing is in progress, the products are held in warehouses or other storage facilities until testing is completed and the products are cleared for shipment. The time required to hold the products while testing for contaminants is known as "micro-hold time," and can cause companies to accrue significant costs relating to warehousing of the products and time lost before the products can be sold and delivered to consumers. Any method that simplifies, accelerates the means of contamination detection, or increases its sensitivity would interest manufacturers. Novel methods of achieving a faster turnaround in obtaining test results in microbiology are typically referred to as "rapid methods."

One current approach to rapid method development in microbiology is to develop and identify methods for detecting molecules that are usually present in all microbial cells, so-called "marker molecules." These marker molecules include, but are not limited to adenylate kinase (AK), alkaline phosphatase (AP), adenosine diphosphate (ADP), and adenosine triphosphate (ATP). These markers can be detected using chemiluminescence, bioluminescence, and other methods. Detection of these marker molecules in a sample can indicate the presence of contaminating microbial cells not only very rapidly, but often with more sensitivity than older, conventional methods. However, oftentimes products to be tested may initially contain a very low number of contaminating microbial cells, and therefore those products have low, even undetectable concentrations of the marker molecules.

Some consumer products, or samples, tested for contamination often require a period of incubation before an analyst can perform a detection assay. Incubation in this case refers broadly to encouraging the growth of contaminating microorganisms in a sample by providing conditions for contamination growth, such as water, nutrients, or a warm environment. Some product types, for example, milk or orange juice, contain sufficient water and nutrients for growth. Merely incubating such product types at a warm temperature is enough to encourage the growth of contaminating microorganisms to rapidly detectable levels. Since products like these are typically supplied in bottles or cartons, the entire bottle or carton is usually incubated intact for convenience before sampling for microbial contamination.

By comparison, other product types, such as household, personal care or pharmaceutical products, are inherently low in water or nutrients. To encourage the growth of any microorganisms within these product types, they must first be dissolved or suspended in a volume of nutrient broth or other appropriate liquid before incubating them at a warm temperature. An example of a typical sample dilution would be the suspension of 1 g product in a volume of 100 ml nutrient broth or other diluent.

Presently, most "rapid detection" methods for determining the presence or absence of microorganisms in chemical, cosmetic, personal care, pharmaceutical, and consumable products can take up to 24 hours, or even longer. A need exists for more rapid methods of detecting microorganisms that can be completed in less than 8 hours, e.g., about 6 hours to about 8 hours, and decrease the so-called micro-hold time are needed. An additional need exists for rapid methods that greatly reduce any factors that might inhibit the detection of microorganisms, yet increase overall detection sensitivity.

SUMMARY

Conventional detection of contaminating microorganisms in highly particulate samples can be improved by significantly reducing the length of time of detection from about 48 hours to 24 hours down to about 8 hours or less using the present detection methods, devices, and systems.

One embodiment of the present method relates to a rapid, sensitive method of detecting the presence of microorganisms in a sample, comprising: obtaining a sample potentially containing microorganisms; optionally diluting the sample in buffer; separating the sample by filtering the sample through a pre-filter for allowing microorganisms and some other materials to flow through; filtering the filtrate from the pre-filter through a filter, where the filter retains the microorganisms, also known as a capture filter; culturing the microorganisms retained on the capture filter; incubating the microorganisms retained on the capture filter with extractant alone or in combination with substrate, where the extractant lyses the microorganisms; filtering the lysed cells through the capture filter; optionally incubating the lysed cell filtrate with a substrate if the substrate was not combined with extractant; adding a detection assay reagent to the incubated substrate mixture; and detecting microorganisms in the sample using a detection device. Alternatively, separation by density may occur by centrifugation with or without the addition of beads. When the contents of the microorganisms, including marker molecules, are simultaneously or subsequently exposed to and incubated with substrate and detection assay reagents, any microorganisms found in the sample may be detected. This process may take fewer than or up to about 8 hours, which is a significant improvement over conventional detection methods.

Another embodiment relates to a filtration device for use in the detection method comprising a vessel for receiving a sample potentially containing microorganisms; a pre-filter for allowing microorganisms to flow through; a capture filter for retaining the microorganisms; and an outlet. The vessel is operably connected to the pre-filter, which is operably connected to the filter, which is operably connected to the outlet through which filtrate flows. A fluid retention element may be used to prevent leakage from the outlet as necessary. An apparatus may also be operably attached to the filtration device to apply positive and/or negative pressure.

A further embodiment relates to a system for determining the presence of microorganisms utilizing the present filtration devices and methods. The system may optionally include a pipette for diluting at least one sample with a buffer; a filtration device; a temperature-controlled chamber for culturing the microorganisms; and a detection device for detecting the presence of microorganisms. One or more of the components of the system may be automated and controlled by a computer or, if desired, operated manually. Additionally, the system may be a high throughput system which facilitates the simultaneous rapid detection of microorganisms in multiple samples.

Yet another embodiment relates to a swab device for detecting microorganisms in a sample potentially containing microorganisms comprising a pre-moistened swab tip, where the swab tip is pre-moistened with an extractant; separate individual compartments of a substrate and a detection assay reagent. Alternatively, combinations of reagents may be held in separate compartments until reactive with the microorganisms or contents of the microorganisms. The swab tip may be exposed to the three reagents separately and sequentially, e.g., the extractant, the substrate, and then the detection assay reagent. The swab device is fashioned in a manner that allows detection of microorganisms by detecting a light signal from a luminescence reaction.

In another embodiment, the present devices and systems may be composed into a kit for detecting microorganisms in a sample, specifically comprising one or more of: a pipette for diluting a sample, a filtration device, a swab device, buffers, growth media, filters, reagents, vessels and containers for amplifying the microorganisms or performing detection assays, vessels and containers for centrifuging the samples, beads, a manifold, and instructions for using and operating the present devices, methods and detection assays. The kit may also contain a vessel for receiving the sample. The components of the filtration device in the kit may be provided in an operably connected configuration, where the vessel is connected to the pre-filter, and which is connected to the filter or as separate components for the user to set up prior to use.

Microorganisms, including bacteria, spores, fungi, yeasts, viruses, molds, or the like, which contaminate chemical (e.g., household cleaners and detergents), cosmetic, personal care, pharmaceutical, and consumable goods in their raw material, in-process, and/or finished product states, need to be detected prior to supplying them to consumers. Thus, the present devices, systems, and methods fulfill the need for rapid, easy-to-perform methods of separating, amplifying, and detecting microorganisms in a shorter time period than previously achievable using conventional methods. The reduction in assay time increases savings to manufacturers of chemical, cosmetic, personal care, pharmaceutical, and consumable goods in their raw material, in-process, and/or finished product states and allows them to provide safe products to consumers in a cost- and time-efficient fashion.

DETAILED DESCRIPTION

Many microorganisms of interest may be found in a variety of samples. These samples may be contaminated with microorganisms such as, but not limited to, bacteria, spores, fungi, yeasts, viruses, molds, and the like. Some of these microorganisms can be difficult to detect in highly particulate and viscous samples. Yet the disclosed methods, devices, systems, and kits are useful in detecting both easy-to-find and difficult-to-find contamination in a variety of samples. One difficult-to-find product type is household products, for example, laundry detergent products with their many particulates that tend to obstruct conventional detection of microorganisms. Other samples in which it is difficult to detect microorganisms by conventional means, and sometimes even by the described filtration methods, include those exhibiting high viscosity and containing high levels of undissolved particles. Such highly viscous samples with undissolved particles rapidly obscure and/or clog filter pores.

The present methods of detecting microorganisms utilize the described devices and systems for testing contaminating microorganisms in various samples. These methods significantly reduce the time required to detect microorganisms compared to conventional methods. The reduction in assay time increases savings to manufacturers of chemical (e.g., household cleaners and detergents), cosmetic, personal care, pharmaceutical, and consumable (e.g., dairy, beverage, etc.) goods in their raw material, in-process, and/or finished product states, and the like. This reduction in assay time also allows for a quicker distribution of safe products to consumers over current methods.

Non-limiting examples of the samples that may be tested include what are considered light beverages (e.g., water, soft drinks, sports drinks, and alcoholic beverages). Other exemplary samples include, but are not limited to, meats and processed foods e.g., fish, poultry and game, meat extracts, preserved, frozen, dried and cooked fruits and vegetables, jellies, jams, compotes, eggs, milk and milk products, edible oils and fats. Staple foods are further non-limiting examples that may be tested e.g., coffee, tea, cocoa, sugar, rice, tapioca, sago, artificial coffee, flour and preparations made from cereals, bread, pastry and confectionery, honey, treacle, yeast, baking-powder, salt, mustard, vinegar, sauces or condiments, spices, and ice. Additional exemplary samples that may be tested include natural agricultural products, e.g., agricultural, horticultural and forestry products and grains, fresh fruits and vegetables, seeds, natural plants and flowers, foodstuffs for animals, and malt. Non-limiting examples of samples that may be tested for microbial contamination include cosmetics and cleaning products e.g., bleaching preparations and other substances for laundry use, laundry detergents, fabric softeners; cleaning, polishing, scouring and abrasive preparations, soaps, body washes, perfumery, essential oils, cosmetics, foundations, creams and lotions, hair lotions, shampoos, conditioners, dentifrices, and toothpastes. Other exemplary samples include, but are not limited to, pharmaceuticals e.g., pharmaceutical and veterinary preparations, sanitary preparations for medical purposes, dietetic substances adapted for medical use, food for babies, plasters, materials for dressings, material for stopping teeth, dental wax, disinfectants, preparations for destroying vermin, fungicides, herbicides, and the like. Any products that should be tested for safety before distribution to consumers are included in the samples that are tested by the disclosed methods. Essentially, any products that are consumed by, applied on, or utilized by consumers are candidates for microbial contamination testing.

The disclosed methods, devices, and systems fulfill the need for rapid, easy-to-perform methods of separating, amplifying, and detecting microorganisms in a shorter time period than previously achievable. Further, testing multiple samples at the same time (leading to high throughput) is also achievable using the present methods, devices, and systems. This rapid and high throughput testing saves companies significant cost and time, allowing them to distribute their products to consumers in a more cost- and time-efficient fashion.

Separation by filtration or centrifugation with or without beads, along with amplification, contribute to the rapid detection of microorganisms using the disclosed methods, devices, and systems. Additionally, the ability of a marker molecule to detect even a single cell within a short period of time, such as the duration of an 8-hour work shift, enables the disclosed method to sensitively and rapidly detect microbial contamination in real-world samples. Filtration or centrifugation concentrates microorganisms into a small, secure volume that can be rinsed to remove traces of the sample, treated with growth culture medium to repair and amplify or increase cell number, and then assayed using various detection methods that recognize the marker molecule found in the microorganisms of interest. Amplification contributes to the rapid detection of microorganisms, not only with respect to the number of microorganisms, but also regarding marker molecules that may be amplified enabling a more pronounced signal in, for example, a luminescent detection method. Prior detection methods failed to recognize the benefits of combining all of these elements, and therefore failed to achieve the present rapid detection methods, devices and systems.

Moreover, the present methods, devices, and systems also provide a sensitive assay which detects low levels of contaminating microorganisms. The disclosed methods advantageously allow for the sensitive and rapid detection of microorganisms in less than about 8 hours, e.g., about 6 to about 8 hours, because the microbial cells are concentrated into a small volume, and then easily detected. Any amplified cells and/or signal would indirectly demonstrate the presence of microorganisms.

The present disclosure may embody many different forms and also may exemplify the principles of one or more of the present methods, devices and systems, without the intention of being limited to the specifically illustrated embodiments.

Method

Separation of Microorganisms from Sample by Filtration

In one embodiment the method of separating microorganisms from a sample utilizes a filtration device comprising a series of filters with decreasing pore sizes. Once a sample potentially containing microorganisms of interest is obtained, the sample may optionally be diluted in buffer as necessary. The sample is then filtered in order to separate the microorganisms from other elements of the sample such as, for example, cellular debris, particulates, etc. The sample first flows through a pre-filter and then a capture filter that retains microorganisms. The pre-filter selectively allows the microorganisms to pass through its filter(s) and yet retain some sample. Once the sample has passed through a pre-filter which allows microorganisms to flow through, the resulting filtrate from the pre-filter then flows through a capture filter which retains microorganisms. The capture filter may have a pore size sufficiently small enough to retain the microorganisms. The pre-filter and/or capture filter may be washed any number of times with buffers that are compatible with the microorganisms after the sample has been filtered. Furthermore, any excess fluid from either the sample or buffer may be purged from the filters using air and/or positive or negative pressure.

Disadvantages of Conventional Separation Techniques

Although binding agents have previously been used in some conventional methods to separate microorganisms from the sample, the instant methods do not require binding agents or supports to which the microorganism and binding agent complex binds. More specifically, binding agents attached to supports were previously used to bind to the microorganisms. In so doing, the microorganisms could be separated from non-microbial particles found in the samples. Anti-body coated beads or microspheres that are functionalized to bind to elements to separate microorganisms from the sample are commonly used separation methods. However, the complexes of binding agents, microorganisms, and supports would inhibit the flow rate and capacity of sample through filters, resulting in clogged filters. Therefore, in order to provide optimal microorganism retrieval from a sample, the present methods do not require any binding agents and/or supports. In fact, the present methods of detecting microorganisms are sufficient to separate the microorganisms from the sample by filtering or centrifuging, without the aid of binding agents and/or supports, through a pre-filter and/or capture filter that retains the microorganisms on the filter.

Cell Culturing Parameters

In the present method any microorganisms retained on the capture filter, which can be as few as about 1 cell or as few as about 10 cells, may be further cultured or grown as needed. As will be understood by those of skill in the art, the culturing conditions may be altered in order to detect microorganisms. The skilled practitioner will appreciate that culturing conditions may be approximated depending on a number of parameters, such as for example, the size of the cells being captured, the species of the microorganisms, and the relative state of health of the cells at the time of filtration (starved/stressed cells are smaller). Although these parameters may be unknown at the time of filtration, those of skill in the art would have sufficient experience having performed numerous tests to assess ideal culturing conditions to yield a sufficient number of healthy cells for detection. The growth medium, nutrient broth, or culture medium (used sometimes interchangeably) may be added to the vessel that receives the sample, either by gravity or by applying positive pressure, results in fully saturating the capture filter while a fluid retention element prevents fluids from leaking through the outlet of the filtration device.

For the filtration method of capturing cells on a filter, cell culturing may be achieved in several ways. Cell culturing may primarily occur on the filter, but for any cells that may be on the surface of the filter, culturing may also occur in the sample receiving vessel. This receiving vessel may also be referred to as an incubation vessel. For example, after filtration and washing, the cells captured on the filter may be grown on the filter itself by adding fresh growth medium and allowing the cells to grow. Alternatively, the capture filter containing cells may be removed from the filtration device and transferred to a separate vessel for cell culturing, which is commonly known in the art as "submerged cultivation". Another embodiment is directed to a "solid phase growth" technique where the filter containing captured cells is wetted with growth medium and incubated in a closed sterile dish in a moisture-controlled environment. A further embodiment relates to washing the filters containing captured cells and then separating the cells from the filters for extraction and detection of marker molecules.

Once a sufficient number of healthy cells have been grown, the capture filter may be returned to the filtration device and the broth containing the cultured cells may pass through the filtration device and original capture filter to concentrate the cells. In another embodiment, the broth containing the cultured cells may pass through a filtration device containing a fresh capture filter. The cells captured on the filter may be further treated in a manner that enhances the detection and/or growth and not limited to the above methods.

The filtration device comprising the capture filter retaining the microorganisms may be incubated at a suitable temperature to encourage the present cells to repair and multiply, if necessary. One of ordinary skill in the art understands that microorganisms grow at different temperatures. For example, some grow between a temperature ranging from about −15° C. to about 122° C., where others grow in the range of about 32° C. to about 38° C., about −15° C. to about 10° C. for cryophiles, and about 45° C. to about 122° C. for thermophiles. Incubation may not be critical, however, depending upon the microorganism of interest. If sufficient healthy cells are present in the initial sample, the method is capable of detecting the healthy cells immediately. On the other hand, this incubation step is generally considered necessary for real-world practical applications, as cells separated from harsh personal care-type products are initially likely to be in a stressed or starved state. Because the cells are concentrated on the final capture filter, and cellular debris has been removed, the time necessary for microorganism growth and/or repair can be reduced to about 1 hour to about 7 hours, where about 4 hours to about 6 hours may be useful to obtain the maximal cells and yet complete the detection method within 8 hours or fewer.

Generally, if retained cells are likely to be in a stressed or starved state as determined by the type of test sample, then they should be incubated in the presence of nutrient broth for a period of not less than 2 hours, which is typically the minimum time required to allow them to repair and recover. However, incubation times may also vary depending on the desired total processing time. The incubation period is greatly reduced when compared to previous conventional assays, because 1) the microorganisms are concentrated into a small volume, 2) the separation of the contaminating microorganisms eliminates sample inhibition of cell repair and recovery, and 3) the separation also eliminates inhibition of detection assay chemistry by removing undesirable marker molecules found in the sample, but which are exogenous to the microorganisms, (e.g., ATP and AK), thereby allowing for cleaner blank controls having a lower luminometric base line. This incubation period allows time for the microorganisms to recover from the filtration processes and grow and divide. Preferably, the microorganisms are grown for as long as necessary to achieve maximal growth of healthy cells necessary for detection. The term "amplification" includes growth and division of microorganisms, as well as the increase in the amount of marker molecules, such as but not limited to, adenosine diphosphate (ADP), adenylate kinase (AK), or adenosine triphosphate (ATP). Because the microorganisms are concentrated by the filtration process and multiply rapidly when compared to other microbial isolation systems, the incubation/growth time is significantly decreased, allowing the total sample testing time to be reduced from about 24-48 hours to about 8 hours or fewer. This reduction in total assay time significantly reduces a manufacturer's micro-hold time and the associated costs.

Any beneficial growth medium or nutrient broth can be used for the cell culturing step. The nutrient broth may be, for example, Letheen broth or any other growth medium that encourages microbial growth. A nutrient broth or growth medium for bacteria may contain, for example, water, a source of carbon and energy, a source of nitrogen, trace elements, and growth factors. The pH of the medium must be established accordingly. Non-limiting examples of nutrient broths or growth media useful in the present methods include Letheen broth, Tryptic Soy Broth, and Fluid Thioglycollate Medium. If captured cells are considered to be in a likely stressed or starved state, then low-nutrient broths (e.g., peptone water) may be used. However, one of ordinary skill in the art would understand how to select an appropriate growth medium for culturing the cells.

Cell Lysis

After the microorganisms are cultured or amplified during the incubation, the cells are lysed and assayed for the presence of marker molecules indicative of the presence of microorganisms in the sample. One of ordinary skill in the art would know that a variety of detection methods may be used to determine the presence of microorganisms and understand how to select an appropriate detection method. The first step for most useful assays includes the lysis of the microorganisms and the subsequent release of the contents of the microbial cells. This cellular material including marker molecules, for example, may be transferred to a detection assay vessel for indirect detection of microorganisms. The detection assay vessel may be, for example, a cuvette or a tube for use in a luminometer. If a micro- or macro-titer plate is used as the filtration device, then the plate may be transferred to a luminometer that specifically reads titer plates. More specifically, after incubating and culturing the microorganisms, the nutrient broth can be purged or removed. Purging the broth is beneficial in that the broth dilution effects are removed as well as any exogenous ATP inhibitory effects. The microorganisms retained on the capture filter can then be subjected to an extractant alone, which lyses the cell membranes of the microorganisms and extracts the contents of the microorganisms, or in combination with a substrate for marker molecule amplification.

In embodiments where the marker molecules are amplified for sensitivity, the cells are preferably subjected to the combination of extractant and excess substrate which lyses the cells and amplifies the cell contents. Lysis or incubation with extractant in conjunction with excess substrate can occur at about room temperature for about 30 minutes to about 120 minutes, preferably for about 1 hour. If sufficient microorganisms are present, however, the marker molecules need not be amplified. An alternative embodiment is directed to flooding the filtered sample containing extraneous marker molecules (e.g., AK) with excess extractant only, expelling and filtering the extractant, and then testing the filtrate containing the cell contents including the cellular marker molecules with a non-amplified ATP-only assay. More specifically, this embodiment, which does not take advantage of marker molecule amplification, incubates the microorganisms at about room temperature with extractant which lyses cells relatively quickly for about 10 seconds to about 5 minutes, preferably about 10 seconds to about 30 seconds. In both embodiments, the extracted cell contents are then expelled or purged through the capture filter into, for example, a cuvette for subsequent luminescence assaying and detection. Alternatively, the extracted cell contents are in a micro- or macro-titer plate for assaying and detection.

The cell contents may contain marker molecules such as, but not limited to, adenylate kinase (AK), adenosine diphosphate (ADP), adenosine triphosphate (ATP), etc. Although mechanical lysis techniques and lysis reagents that only destroy the cell membranes are useful, chemical lysis reagents are preferred. Lysis techniques and reagents such as detergents commonly used in the field may also be useful in the present methods. Non-limiting examples of extractants/lysis agents include detergents (e.g., cationic, nonionic and zwitterionic detergents, such as, CHAPS and the Triton-X series of nonionic detergents) and antibiotics, and these agents can be commonly used for these lysis purposes. These lysed cell contents, including the marker molecules, are typically passed through the capture filter that retains microorganisms and collected for subsequent assay (amplified or non-amplified).

Marker Molecule Amplification and Detection

After lysis and exposure of the marker molecules of the microorganisms, the marker molecules may be amplified by incubating the filtrate with a suitable substrate. Supplying the filtrate with excess substrate will result in the amplification of one of the marker molecules, thereby resulting in an amplified signal in the detection assay for determining the presence of microorganisms. The filtrate may be incubated at about room temperature to about 35° C. with excess substrate for about 5 minutes, about 30 minutes, about 40 minutes, about 60 minutes, or longer. The time can be increased to any length to increase the sensitivity if necessary. However, incubation times are variable, oftentimes dictated by throughput requirements and result time-pressure from the user. A longer incubation time will (while unconverted substrate remains) convert more microbial cell contents to detectable signal, thereby affording increased sensitivity. Incubation times may range from about 5 minutes to about 120 minutes, preferably ranging from about 30 minutes to about 60 minutes. Alternatively, the extractant and substrate are simultaneously incubated with the microorganisms retained on the filter under the same conditions as described above. After a sufficient amount of time, where the cell membranes of the microorganisms have been destroyed and the contents of the microorganisms, specifically the marker molecules, have been exposed to excess substrate, the lysed cells may be filtered through the final capture filter that retains microorganisms.

A detection assay for indirectly determining the presence of microorganisms after or simultaneously during lysis can also be applied. One detection assay that is particularly useful for detecting the presence or absence of microorganisms is an ATP bioluminescence assay. ATP bioluminescence assays are an industry standard that is capable of generating fast, reliable, and accurate results for microbial limits in chemical, cosmetic, personal care, pharmaceutical, and consumable goods in their raw material, in-process, and/or finished product states. This system eliminates subjectivity and provides definitive and reproducible results. This assay allows for the production of large quantities of "amplified" ATP by using an adenylate kinase (AK)-catalyzed reaction as follows:

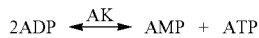

The subject method can apply this reaction by utilizing the AK found in the cells of the microorganisms and adding to the lysed cells excess ADP substrate in order to drive the reaction towards generating ATP. After a short period of time, the ATP level can increase by about 1000 times. In a preferred embodiment, the extractant and substrate are simultaneously incubated with the contents of the microorganisms, e.g., marker molecules, for a sufficient period of time to produce amplified ATP. The period of time may be rapidly from about 5 minutes to about 1 hour and occur with ease at about room temperature. The ATP is then reacted with a detection assay reagent, (e.g., luciferin/luciferase) and measured based on the typical luciferase reaction as follows:

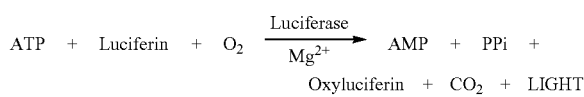

Measurable light emission can indirectly indicate the presence of microorganisms. In addition, the level of microbial contamination can be quantified by the amount of light given off by the test sample. The test results can be read using a detection device, such as for example, a luminometer. This light-emissions assay can be useful for microbial limit testing, in-process sterility testing, bulk or raw material testing, environmental monitoring media fills, and antimicrobial effectiveness studies. As with all assays, known positive, negative, and reagent control samples are also included for comparing against the test sample. A positive result is typically determined in a few ways. If the test sample emits an amount of light equivalent to or greater than about two times, or any of a wide range of statistically valid interpretive methods, as compared to the amount of light emitted by an identical, cell-free control sample run simultaneously, then a positive result is likely present. Alternatively, if fresh cell-free control samples are unavailable, a fixed-integer "cutoff" result may be pre-established by prior analysis and used to adjudicate the positive/negative status of subsequent samples. Prior analysis would ideally consist of testing no fewer than, for example, about 30 real-world cell-free samples (where a known amount of microorganisms are not added and the samples are assumed to be free of contaminating microorganisms). Testing would preferably occur at a customer site or facility to reduce the possibility of contamination during a transfer of samples and then the results would be averaged to create an average value. A subsequent test of a sample producing about >2 times this average value would typically be considered positive for contaminating microbial cells.

In another embodiment, the detection assay may be a chemiluminescent assay, a bioluminescent assay, a nucleic acid hybridization assay, or the like. If a chemiluminescent or bioluminescent assay is employed, then the assay comprises the steps of adding at least one chemiluminescent or bioluminescent reagent to the assay solution, and detecting the presence or absence of a chemiluminescent or bioluminescent signal, where the signal indicates the presence of microorganisms and the absence of the signal indicates the absence of microorganisms.

If a nucleic acid hybridization assay is used, the probe can be designed to detect deoxyribonucleic acid (DNA), messenger ribonucleic acid (mRNA), or ribosomal ribonucleic acid (rRNA). Such an assay can comprise the steps of adding at least one nucleic acid probe capable of detecting microbial nucleic acids, such as, but not limited to, rRNA to the assay solution under hybridizing conditions. After hybridization, a user can detect the presence or absence of a hybridization signal, where a hybridization signal indicates the presence of microorganisms and where the absence of a hybridization signal indicates the absence of microorganisms.

Other assays that may be employed include any known method of detection. These methods include, but are not limited to, protein assays (e.g., fluorescence assays, antibody assays, and enzyme-linked immunosorbent assays (ELISAs)), colorimetric assays, redox measurement, impedance measurement, acid/alkali detection, polymerase chain reaction (PCR), real-time polymerase chain reaction (rt-PCR), fluorescence in situ hybridization (FISH), surface plasmon resonance and lateral-flow assays.

One of ordinary skill in the art would know how or be able to determine the appropriate assay parameters useful for all of the above-listed assay types. This knowledge includes, but is not limited to chemiluminescent assays, bioluminescence assays, nucleic acid hybridization assays, protein assays, ELISAs, colorimetric assays, redox measurement, impedance measurement, acid/alkali detection, PCR, rt-PCR, FISH, surface plasmon resonance and lateral-flow assays.

For testing products and samples that are viscous or thick, it is usually beneficial to initially suspend the sample in a buffer or other diluent prior to filtration. For example, 1 g of the sample may be suspended in a buffer or other diluent to a final volume of between about 5 ml and about 25 ml, preferably between about 10 ml and 15 ml, and most preferably to a final volume of about 10 ml. The buffer can be any buffer that has a pH in the physiological range (e.g., about pH 7) including, but not limited to deionized water, a Tris buffer, phosphate buffered saline (PBS), a microbial growth medium, or any buffer that is compatible with the sample and does not detrimentally affect the sample in any way.

A further embodiment of the methods, devices, and systems relates to the three reagents: extractant, excess substrate, and detection assay reagents. The microorganisms retained on the capture filter may be exposed to these reagents collectively, sequentially, or in various combinations. For example, all three reagents (i.e., the extractant, substrate, and detection assay reagents) may be combined and added to the microorganisms; all three reagents may be added one at a time; the extractant and substrate reagents may be combined followed by exposure to the detection assay reagent; or the extractant may initially be added then followed by exposure to the combination of substrate and detection assay reagents, and then detected using any one of a variety of detection assays. Alternatively, in the embodiment that does not require amplifying marker molecules, the extractant and detection assay reagents would be used without excess substrate. One method of detecting microorganisms in a sample potentially containing microorganisms may comprise filtering the sample through a pre-filter for allowing microorganisms to flow through; filtering the pre-filter filtrate through a capture filter for retaining microorganisms; culturing the microorganisms retained on the capture filter; incubating the microorganisms retained on the capture filter with extractant in combination with a substrate, such as adenosine diphosphate; filtering the lysed cells through the capture filter; adding a detection assay reagent, such as luciferin/luciferase, to the capture filtered lysed cells; and detecting microorganisms in the sample using a detection device, such as a luminometer.

Separation of Microorganisms from Sample by Centrifugation

Another embodiment is directed to a method of separating by centrifugation. Because samples that are highly viscous or those that have high levels of undissolved particles readily obstruct flow through filters, separation by centrifugation may be more preferred for these types of samples. Since these types of samples often have particulate sizes similar to those of microbial cells, filtration by size exclusion does not distinguish between the sample particulates and the contaminating microorganisms. However, centrifugation separates particulates by density, thereby allowing the separation of similarly sized particles.

Due to the viscosity and/or highly particulate nature of the types of samples that are preferably separated using centrifugation, samples are preferably initially diluted in a buffer that is appropriate for the sample. Dilutions may be in the range of from 1:10 to 1:100,000. In one embodiment, a 10% w/v diluted sample is centrifuged at a speed of 2000×g (i.e., 2000 times the force of gravity) for fifteen minutes at room temperature. These parameters may change depending on the sample, so long as the cells are sedimented to the sides or bottom of the container in which they are spun. One of ordinary skill in the art would understand how to select appropriate buffers and containers for centrifugation; however, polypropylene 15-50 mL conical-bottomed centrifuge tubes are exemplary containers. After centrifugation, the supernatant is discarded, leaving the sedimented cells behind.

The cells are washed in a buffer and spun again to remove any residual material. For example, the cells are washed with an equal volume of appropriate buffer, spun at the same settings as described above, and the supernatant is discarded, leaving pelleted washed cells. Although the cells may be assayed for detection of contaminating microorganisms, an alternative embodiment is directed to culturing the cells in a small volume of growth medium, nutrient broth, or culture medium which is added in an amount of, for example, about 1-3 mL. After vortexing at room temperature for about 10 seconds or a sufficient time period to mix the cells and growth medium, the cells are then incubated preferably at about 30° C.-32° C. for about 8 hours or less or about 4 hours or less. The culturing parameters are similar to those previously described above. The ordinarily skilled practitioner in the art would appreciate that the incubation period will be sufficient to amplify or culture the cells into a healthy robust state after having been starved or stressed by centrifugation. An appropriate growth medium may be selected from those previously described. After a sufficient amount of time has passed, the incubated cells are centrifuged for 15 minutes at 2000×g at room temperature. The supernatant is discarded leaving only the pelleted cells. The cells are then subjected to lysis by the addition of extractant and also substrate followed by assaying for the presence of marker molecules and/or a light signal in luminescent detection assays that are indicative of the presence of microorganisms in the sample.

In particular, the pelleted cells are vortexed at room temperature for about 10 seconds or until the cells are mixed with extractant alone or in combination with excess substrate. In order to amplify the marker molecule so that low levels of microbial contamination may be detected in the sample, the mixture is incubated for about 1 hour or less. The contents are then transferred to a detection assay vessel for reading by a luminometer. The detection (luminescence) assay reagent may be added either manually or automatically by the luminometer prior to reading for relative light units. Control samples are also utilized for comparison and confirmation that the assay properly worked.

One method of detecting microorganisms in a sample potentially containing microorganisms may comprise diluting the sample; centrifuging the sample to form a cell pellet; discarding supernatant of centrifuged sample; washing the cell pellet by resuspending the cell pellet in buffer, centrifuging the resuspension, and discarding the supernatant; culturing cells in growth medium; centrifuging the cultured microbial cells; discarding supernatant of centrifuged cultured microbial cells; incubating the microorganisms or microbial cells with extractant in combination with a substrate, such as adenosine diphosphate; adding a detection assay reagent, such as luciferin/luciferase, to the incubated extractant and substrate sample potentially containing microorganisms or microbial cells; and detecting microorganisms in the sample using a detection device, such as a luminometer. One of ordinary skill in the art would understand that multiple washes including resuspending cells in buffer followed by centrifugations and removal of supernatants may occur in order to remove extraneous debris.

In another embodiment, the above centrifugation assay may occur with the addition of beads or similar microspheres that are approximately the same size and density as microbial cells. The beads sediment at about the same rate as the microbial cells when centrifuged, The beads are believed to assist in the attachment of microbial cells to the walls or sides of a container in which the sample is centrifuged, as well as provide a visible pellet enabling the practitioner to see and collect the microbial cell pellet. Visibility of the pelleted cells provides another benefit to the practitioner who may safely avoid vacuum suctioning or pipetting out the cells during removal of the supernatant.

Non-limiting examples of beads that are useful include non-functionalized beads or microspheres (e.g., without any attachments, coatings, or special properties). Examples of beads that are not used in the described methods include functionalized, magnetic, paramagnetic, or antibody-coated beads, or beads that are for immobilization, such as for covalently coupling proteins, peptides, nucleic acids, and the like.

Samples that are toxic or have a tendency to lose cells when decanting can significantly benefit from the centrifugation with beads method. The beads or microspheres may be made out of a variety of materials commonly known and used in the art. For example, polystyrene microspheres (Bangs Laboratories; PS03N/6560) or beads of similar material that are approximately the same size and density as microbial cells are useful. The beads are added to the sample at levels typically between about 0.05% and about 0.01% (w/v). One of ordinary skill in the art appreciates that the dilutions are dependent on the type of sample and may be easily adjusted. Controls without beads and with buffer alone are simultaneously used for comparison. The diluted test sample is initially centrifuged at a speed of 2000×g for about 15 minutes in the presence of beads. The supernatant is removed. Buffer is added to the cell pellet in order to rinse the cells. The resuspended sample with beads is centrifuged at 2000×g for about 15 minutes. The supernatant is discarded. Growth medium or nutrient broth is added to resuspend the cell pellet followed by vortexing to mix for about 10 seconds at room temperature. The cell mixture is incubated at about 30° C.-32° C. for approximately 8 hours or less while shaking Shaking is recommended to mix the cells with growth medium broth nutrients and prevents sedimentation with non-nutrient particles. For example, shaking may occur on an orbital shaker at about 200 rpm. Incubation occurs for a period of time to enable the cells to grow and recover from stress. Once a sufficient number of healthy cells have grown, the cells are centrifuged at about 2000×g for about 15 minutes, and the supernatant is then discarded. A 1:1 mixture of extractant and substrate is added to resuspend the cellular pellet and mixed by vortexing for about 10 seconds at room temperature. After vortexing, the sample is incubated at room temperature to amplify released marker molecules (e.g., ATP). Marker molecule amplification may occur during an incubation period ranging from about 5-120 minutes, preferably about 60 minutes, as previously described. The mixture is then transferred to a detection assay vessel or a cuvette, for example. Prior to reading the contents of the detection assay vessel in a luminometer, a detection assay reagent is added that induces the luciferase reaction to emit a light in the presence of microbial ATP, for example. Although the beads remain in the reaction that is read in the luminometer, they are inert and thus exert no adverse chemical effect on the amplification and detection steps. They are also not present in sufficient amounts to exert any significant blocking or inhibitory effect on generated light.

One method of detecting microorganisms in a sample potentially containing microorganisms may comprise diluting the sample; centrifuging the sample with beads to form a cell pellet; discarding supernatant of the centrifuged sample; washing the cell pellet by resuspending the cell pellet in buffer; centrifuging the washed cell pellet and beads; discarding the supernatant of the centrifuged pellet and beads; culturing cells in growth medium; centrifuging the cultured cells and beads; discarding supernatant of centrifuged cultured cells; incubating the microorganisms or microbial cells of the sample with extractant in combination with a substrate, such as adenosine diphosphate; adding a detection assay reagent, such as luciferin/luciferase, to the incubated extractant and substrate sample potentially containing microorganisms or microbial cells; and detecting microorganisms in the sample using a detection device, such as a luminometer. One of ordinary skill in the art would understand that multiple washes including resuspending cells in buffer followed by centrifugations may occur in order to remove extraneous debris.

Filters

In order to detect microorganisms, the microorganisms must first be separated from the sample. Essentially, the sample is filtered to remove sample components and capture contaminating microorganisms using a single or multiple filters. However, this can be difficult if the sample contains insoluble or particulate material, which may rapidly clog the pores of the filter designed to capture and retain microbial cells. One way of separating the microorganisms is by using differential filtration through a series of filters designed to retain dispersed insoluble or particulate material from the sample, but allow free passage of microbial cells. This separation is achieved through the use of pre-filters with carefully-selected pore sizes. The pre-filter may be one filter of at least a double-layer of filters or at least two separate filters, both of which have filters of decreasing pore sizes which allow passage of microorganisms and other components of the sample smaller than the pore size. The filters of the pre-filter may have a pore size larger than microorganisms such that cellular debris are separated from the smaller microorganisms. Pre-filter filtration steps, when necessary, can result in a cleaner and more concentrated cell preparation, and significantly increase the volume of filterable sample. This is of enormous benefit to manufacturers and practitioners, who typically wish to test as large a volume of sample as possible. Alternatively, a single filter may be used in the pre-filter if the sample is relatively "clean".

The pre-filter used in the present methods reduces the risk of filter clogging, allows for the capture of large molecules and compounds found in the sample, and allows for the passage of microorganisms. Once the insoluble or particulate matter of the sample has been separated from the sample, the subsequent capture filter that retains the microorganisms enables the microorganisms to be amplified and tested in their entirety and in the absence of non-microbial particulate materials, thereby greatly increasing overall sensitivity of the detection method. The combination of pre-filter and capture filter allows the resulting microbial cells on the filter to be essentially free of extraneous cellular debris or non-microbial particles, thereby facilitating the rapid, sensitive detection of microorganisms. Alternatively, if the sample is relatively "clean," a pre-filter can be unnecessary.

Although the pore size of the pre-filter filters may vary depending on the size of the potential microorganisms, the pre-filter filters may have, for example, a pore size ranging between about 5µ and about 100µ, which allows the passage of microorganisms. Preferably, a first filter of a double-layer of filters or the first filter of the pre-filter may have a pore size ranging between about 20µ to about 100µ. A second filter of the double-layer of filters of the second filter of the pre-filter may preferably have a pore size ranging between about 5µ and about 10µ, which also allows the passage of the microorganisms.

One of ordinary skill in the art would understand how to select filters of the appropriate size depending on the size of the microorganisms that are potentially in the sample. A pre-filter having filters with a pore size of greater than, for example, 5µ allows microorganisms smaller than 5µ, such as those belonging to the genus *Escherichia, Salmonella, Shigella,* or *Burkholderia,* will allow those types of bacteria to pass through the pre-filter. However, in order to retain microorganisms on the subsequent capture filter, the pore size of the capture filter should be smaller than the size of the microorganisms, for example, ranging between about 0.2µ to about 4µ. Additional capture filter pore sizes that are useful in the described filtration method include pore sizes of about 0.45µ and about 0.7µ. A filter of 0.45µ is a commonly used pore size for trapping bacteria. A filter of 0.2µ is considered to be a "sterilizing grade" pore size that is small enough to retain all cell sizes. However, such small pores can rapidly clog, even with relatively particle-free filtrate from the pre-filter. In such cases, the capture filter can have a slightly increased pore size to compensate one that retains more than about 90% of cells presented to it.

In one embodiment of the present method, a capture filter, which retains microorganisms larger than 0.7µ, having a pore size of 0.7µ can be used. A pore size of 0.7µ has a good tolerance for the remaining small non-microbial particles that pass through the pre-filter. This method enables sufficient sample amounts to pass through the capture filter, yet still retain >90% of any microbial cells. One of ordinary skill in the art would select the appropriate sized filters based on size exclusion in order to retain microorganisms from a sample onto a capture filter as practiced in the present methods, devices, and systems.

The filters of the subject methods, devices, and systems may be composed of a wide variety of materials including, but not limited to plastics, polymeric material, polyester, nylon, glass fibers, polypropylene, polycarbonate, polyethersulfone, polyether ether ketone (PEEK), polyvinylidene fluoride, cellulose, cellulose derivatives, ceramic, and the like. The filters may be individual filters or those found in columns, syringes, and/or plates. The filters are available to purchase from companies such as MILLIPORE™, SPECTRUM® Laboratories, Inc., PALL™ Corporation, and Small Parts an AMAZON™ Company. Polyester is one useful material because other materials can sometimes bind the very compounds to be detected (e.g., marker molecules) and polyester is a cleanable, autoclavable material.

Although positively-charged filters generally could be used to retain microorganisms on the capture filter with high efficiency, they are currently not preferred in some instances. Should positively-charged filters that retain microorganisms with relatively little cellular debris, such that the cellular debris does not interfere with the detection of microorganisms be available, those positively-charged filters would be useful in the inventive method and devices. A positively-charged filter essentially binds all of the microorganisms in a sample because microorganisms are inherently negatively charged. Since the microorganisms would be retained on the filter by charge, the pore size of the filter would be a secondary consideration, i.e., filter pore sizes larger than the microorganisms could be used. Yet, utilizing a positively-charged filter with a pore size less than the size of the microorganisms would doubly ensure that the microorganisms are retained on the capture filter.

Without being bound by theory, because filter membranes often possess a characteristic known as "anisotropy," where the properties of the filter membranes are directionally-dependent, directionality of the sample flow is important. For example, in a syringe in the upright position, where the plunger tip is closest to the top surface of the filter membrane, the pores of the top surface of the filter membrane closest to the inlet where a sample first flows through are larger than the pores of the underside of the filter membrane closest to the outlet through which the sample is purged. Many filter membranes may not wet freely to adsorb reagents and often require the addition of wetting agents in order to properly function. However, such wetting agents can be washed out during the first (sample) filtration and may not even be present when subsequent reagents are added. Thus, subsequent reagents that are added or filtered through result in beading on the filter surface and hardly penetrate the filter membrane. Since the cells are embedded within the filter, the reagents cannot effectively penetrate the filter membrane and thus do not necessarily interact with the cells.

Filtration Device System

The filters of the subject methods, devices, and systems can be arranged in a filtration device. A preferred filtration device includes: a) a vessel for receiving a sample potentially containing microorganisms; b) a pre-filter for allowing the passage of microorganisms; c) a capture filter for retaining microorganisms; d) an outlet; and e) a fluid retention element. The vessel is operably connected to the pre-filter, which is operably connected to the capture filter, which is operably connected to an outlet through which filtrate flows. The fluid retention element may be a cap or a covering that attaches to the outlet when solutions or fluids are in the vessel, pre-filter, and/or capture filter in order to prevent fluid leakage from the outlet. The fluid retention element is used as necessary and may be removable. The filters may be arranged in sequential order from the vessel that receives the sample. Alternatively, the filters may be arranged sequentially within the vessel itself, as long as the order of filtration steps, is the same, i.e., the sample loaded in the vessel filters through the pre-filter and then the capture filter.

The filtration device may be in the form of a syringe utilized in the upright position, where the barrel forms the vessel for receiving a sample potentially containing contaminating microorganisms. Accordingly, the vessel is operably connected to a pre-filter, which is operably connected to a capture filter that retains microorganisms, which is operably connected to an outlet from which liquids (e.g., sample, media, buffers, reagents) may pass. A positive pressure may be applied to the sample by pushing the sample through the series of filters, for example, by using a syringe's plunger which pushes the sample through the vessel to the filters. Alternatively or additionally, a negative pressure can be applied to the sample via, for example, a vacuum, which pulls the sample through the series of filters via the outlet. The vacuum may be attached to the outlet that is operably connected to the final capture filter that retains microorganisms.

Systems

In another embodiment, the subject methods, devices, and systems also relate to a system for determining the presence or absence of microorganisms comprising: optionally, a pipette for diluting at least one sample with a dilution buffer as necessary; a filtration device as described above; a temperature-controlled chamber for culturing or amplifying the microorganisms; a detection device for detecting the presence or absence of microorganisms. The system may further comprise an apparatus comprising a positive pressure device and/or a negative pressure device for applying pressure to the filters of the filtration device.

Another embodiment of the system is an automated system. The present system may additionally comprise a computer for operably connecting and controlling the pipette, the filtration device, the temperature-controlled chamber, and the detection device to form an automated system. One or more of the components of the automated system can be controlled by the computer or, if desired, operated manually.

A further embodiment may be directed to a high throughput filtration system which allows multiple samples to be simultaneously tested for potentially contaminating microorganisms. Multiple filtration devices may be attached to a manifold which is attached to, for example, a vacuum trap and apparatus, so that the negative vacuum pressure is applied to each of the multiple samples being tested for microorganisms. Alternatively, positive pressure may be asserted on each of the samples, pushing them through each of the filtration devices, rather than pulling the samples by negative pressure through the filters. An example of a positive pressure system can be, but is not limited to, a plunger or similar instrument, which can force the samples through the sequentially situated filters, i.e., through the pre-filters and then the capture filters.

The high throughput filtration system may also comprise a filtration device such as a macro- or micro-titer plate that has the aforementioned series of filters. The high throughput method of detection would essentially be performed similarly to the present methods utilizing a single filtration device. However, the detection device selected for reading the samples permits reading macro- or micro-titer plates. When fluid growth media or reagents are held in the macro- or micro-titer plates, the fluid retention element may be a fluid retention covering instead of the fluid retention cap used in conjunction with the syringe embodiment of the filtration device described above. Alternatively, after any one of the post-lysis steps, the filtrates may be transferred to another vessel for performing the marker molecule amplification step, the detection assay step, and/or the detection device reading step.

Swab Device

Yet another embodiment relates to a swab device for detecting microorganisms in a sample potentially containing microorganisms. The swab device comprises a pre-moistened swab tip and reagents that are separately contained and sequentially delivered to the swab tip and/or fluid in which the swab tip sits. The three reagents, as also used in the present methods, include: an extractant for lysing and releasing marker molecules from the cells of the microorganisms; excess substrate; and detection assay reagents.

The swab tip may be pre-moistened with a buffer, growth media, or extractant in order to collect the sample which may potentially contain microorganisms. One benefit of using a swab device is the rapid determination of the presence of microorganisms by swiping a small test sample. After sample collection, the swab tip is returned to the swab device immediately after swabbing or after a minimal delay. However, the swab tip may be assayed directly or incubated with the collected microbial cells for minutes to about 24 hours or more as necessary depending on the sensitivity requirement. The swab tip may then be exposed to extractant which is separately housed from the other reagents in the swab device. Lysis of the cell membranes of potential microorganisms occurs, which may result in some of the marker molecules settling in the fluid in which the swab tip sits, or in this step, extractant. Alternatively, if the swab tip was pre-moistened with extractant, then the substrate, which may be separately housed in the swab device from the other reagents, may be released to contact the swab tip and/or fluid in which the swab tip sits. Afterwards, the swab tip and/or fluid in which the swab tip sits, or in this step, the collection of extractant and substrate, is exposed to the detection assay reagent, also initially separately housed in the swab device. Once the swab tip has been sufficiently exposed to all of the reagents, the swab tip, fluid in which the swab tip sits (e.g., extractant, substrate, and detection assay reagent), and/or swab device is transferred to a detection device that can read the test results, such as for example, a luminometer when the detection assay is based on luminescent assay. Preferably, the swab device is fashioned in a manner that allows for indirect detection of microorganisms by detecting a light signal resulting from a luminescence reaction via a luminometer.

In one particular embodiment, the swab device may have separate chambers for each of the reagents. After collection of the sample potentially containing microorganisms, the swab tip may contact or be saturated with extractant. The substrate may then be released by mechanically activating a component of the swab device. For example, the swab device housing the substrate may be partially bent breaking a barrier to release the substrate to flow down the swab device towards the swab tip. The substrate may settle in a collection of extractant or soak the swab tip exposed to extractant. The swab device may be constructed such that when force is applied, the swab tip may "punch" through a barrier that separates, for example, the detection assay reagent from the other reagents, thereby exposing the swab tip and collection of extractant and substrate to detection assay reagent. The volume of reagents, incubation times, and incubation temperatures can be established prior to use and should generally follow those in the present method.

Method of Detection Using Swab Device

The swab device may be used in the method of detecting microorganisms in a sample. A sample is obtained by swiping the pre-moistened swab tip onto an area to collect a test sample potentially containing microorganisms. The swab tip is pre-moistened with buffer or growth medium to aid in the collection of test sample. In another embodiment, the swab tip is pre-moistened with extractant. Once the test sample has been collected, the swab tip may be incubated at a suitable temperature to encourage the present cells to repair, amplify, and grow from, for example, about a few seconds, minutes, one hour, up to 24 hours if necessary. This incubation step can be unnecessary, however, if healthy cells are present in the initial test sample collected on the swab. The swab tip containing the microorganisms from the sample contacted with extractant for lysis to occur may be incubated for about 10-30 seconds, or longer (e.g., about 5 minutes, about 10 minutes, or about 30 minutes to about 1 hour) at about room temperature. Alternatively, the swab tip can be incubated with extractant and substrate for lysis and marker molecule amplification. The detection assay reagent can then be added to the swab tip and/or fluid in which the swab tip contacts. After following the directions in the appropriate detection assay, the swab tip and/or fluid in which the swab tip contacts can then be transferred to a detection device, preferably, a luminometer that may read the results from the swab tip, swab device, and/or fluid in which the swab tip contacts.

Kit

The present devices and systems may be included in a kit for separating and/or detecting microorganisms from a sample comprising one or more of: the present devices (e.g., filtration, centrifugation and/or swab devices); buffers; growth media; filters, reagents: extractant, substrate, and detection assay reagents; beads; and any other components described in the present methods, devices, and systems. The filtration device of the kit may be provided in an operably-connected configuration, as described herein, or as separate components for the user or practitioner to set up prior to use. The kit may also contain instructions for using and operating the present devices and detection assays for separating and detecting microorganisms.

The kit may also contain vessels for receiving the sample and/or vessels for use when centrifuging, amplifying the microorganisms, or performing the detection assays. The components of the kit can be provided in operably-connected configurations, or as separate components for the user to set up prior to use. In one embodiment, the filters are sequentially connected to the outlet of a vessel that receives the sample. In another embodiment, the filters are sequentially connected, but within the vessel itself. The kit can further include a manifold for processing multiple samples at one time, both automatically and manually.

Applications

The present methods, devices, and systems may be used to test for contamination in chemical, cosmetic, personal care, pharmaceutical, and consumable goods in their raw material, in-process, and/or finished product states. In their various states these goods, may be contaminated by a variety of microorganisms, including bacteria, spores, fungi, yeasts, viruses, molds, and the like. A need exists for a rapid and sensitive test method for detecting any contaminating microorganisms in these products in order to prevent shipment of unsafe products to consumers. Since these products are typically manufactured in bulk and each lot needs to be tested until clearance of safe products before shipment, costs accrue for the storage of these products and any delay in shipment. However, the present methods, devices, and systems allow for a rapid and sensitive testing process which requires about 8 hours or less, enabling the prompt turn-around from manufacture to delivery of products.

In one embodiment, the methods may be used to detect viruses. For example, the method can detect viruses including, but not limited to, influenza viruses, human immuno-deficiency viruses, measles viruses, hepatitis viruses, noro-viruses, rotaviruses, herpes viruses, and rubella viruses. In another embodiment, the present methods, devices, and systems may be used to detect yeasts, including, but not limited to, *Candida* species and *Saccharomyces* species. Yet a further embodiment is directed to detection of gram negative bacteria. For example, the gram negative bacteria may be, but is not limited to *Escherichia* species (*E. coli*), *Acinetobacter* species (*A. baumannii*), *Salmonella* species, *Burkholderia* species (*B. cepacia*), *Shigella* species, Ralstonia species (*R. pickettii*), and *Pseudomonas* species (e.g., *P. alcaliphila* and *P. aeruginosa*). In another embodiment, gram positive bacteria may be detected, such as but not limited to, *Bacillus* species (e.g., *B. cereus* and *B. thuringiensis*). Another embodiment is directed to the detection of bacterial spores, such as gram-positive *Lysinibacillus sphaericus*.

EXAMPLES

Example 1

Sensitivity Assay of Controlled Microbial Samples

Controlled experiments were performed in Ringer buffer to detect assay sensitivity. Ten (10) mL of Ringer buffer and 10 mL of Ringer buffer spiked with a known amount of microorganism were each separately filtered through different 10 mL syringes fitted with a 0.45μ disc filter (filtration device) for the assay blank control and the assay sample, respectively, by applying positive pressure using the syringe plunger. The filters were washed with 20 mL of Ringer buffer. Three (3) mL of Letheen broth were added, 2 mL of which were filtered through and 1 mL was separately retained, followed by immediate capping of the disc filter outlet tip with a fluid retention element to prevent leakage of liquids. The entire syringe device or filtration device was incubated upright at 32° C. for 6 hours, where the capped outlet was positioned below the capture filter that retains microorganisms, which was positioned below the vessel for receiving a sample or control. After incubation, the fluid retention element was removed, the broth was purged, and the plunger was removed from the vessel of the syringe. The outlet positioned below the filter disc was again capped and 300 μL of the extractant and substrate ADP solution was added. The filtration device was incubated upright at room temperature for one hour. At the completion of the incubation period, the fluid retention element was removed and the contents were expelled into an assay cuvette. The cuvettes containing controls and samples were placed in a CELSIS ADVANCE™ Luminometer and injected with 100 μL of luciferase reagent to detect the amount of ATP produced by the adenylate kinase reaction. The emission of light was detected as Relative Light/Luminescence Units (RLU). Detection of ATP indicated the presence of microbial contamination in the tested sample using adenylate kinase as a marker. In order to detect the sensitivity of the assay in Ringer buffer, various organisms grown in Letheen broth for 24 hours were diluted to have 100 CFU (Colony Forming Unit) per mL followed by a twofold dilution to theoretical 1 CFU or less cells per mL. The diluted cells were spiked into Ringer buffer to determine the limits of detection and signal to noise ratio. Corresponding unspiked sample was treated as a reagent blank. The cell counts were confirmed by plating on tryptone-soy agar plates. Triplicate values were generated and average values were expressed with standard error. The data of Table 1 and Table 1A depict the limits of detection together with signal to noise ratios for various organisms in Ringer buffer. The asterisk (*) represents those values that are the average of three observations.

TABLE 1

| | A. baumannii | | | B. cepacia | |
|---|---|---|---|---|---|
| CELLS | MEAN RLU* | S/N RATIO* | CELLS | MEAN RLU* | S/N RATIO* |
| 0 | 328 | — | 0 | 368 | — |
| 0.8 | 3206 | 10 | 3 | 1772 | 5 |
| 1.5 | 8607 | 26 | 5 | 3800 | 10 |
| 3.0 | 100956 | 308 | 11 | 9938 | 27 |
| 6.0 | 237538 | 724 | 21 | 112654 | 306 |
| 12.0 | 337655 | 1029 | 42 | 21269 | 58 |
| 25.0 | 834253 | 1696 | 85 | 185247 | 503 |
| 50.0 | 1188121 | 3622 | 169 | 196175 | 533 |
| | | | 338 | 249689 | 966 |

TABLE 1A

| CELLS | MEAN RLU* | S/N RATIO* | CELLS | MEAN RLU* | S/N RATIO* |
|---|---|---|---|---|---|
| | B. cereus | | | B. thuringiensis | |
| 0 | 554 | — | 0 | 125 | — |
| 0.06 | 11678 | 21 | 1.25 | 140 | 1 |
| 0.13 | 54186 | 98 | 2.5 | 3367 | 27 |
| 0.25 | 54849 | 99 | 5 | 46563 | 373 |
| 0.50 | 36248 | 65 | 10 | 153494 | 1228 |
| 1 | 165589 | 299 | 11 | 344493 | 2756 |
| 2 | 535181 | 966 | 20.5 | 657825 | 5263 |
| 4 | 579114 | 1045 | 41 | 1245183 | 9961 |
| 8 | 1147904 | 2072 | | | |
| | L. sphaericus | | | P. alcaliphila | |
| 0 | 978 | — | 0 | 202 | — |
| 1 | 8010 | 8 | 1 | 11652 | 58 |
| 2 | 14170 | 14 | 3 | 8180 | 40 |
| 5 | 47700 | 49 | 5 | 73380 | 363 |
| 10 | 235535 | 241 | 11 | 50967 | 252 |
| 19 | 237810 | 243 | 22 | 100668 | 498 |
| 39 | 415906 | 425 | 43 | 523582 | 2592 |
| 77 | 767595 | 785 | 86 | 682224 | 3377 |
| 154 | 1119925 | 1145 | 172 | 48619 | 241 |
| | P. aeruginosa | | | R. pickettii | |
| 0 | 201 | — | 0 | 638 | — |
| 1 | 533 | 3 | 0.59 | 406 | 0.64 |
| 2 | 1345 | 7 | 1 | 808 | 1.27 |
| 5 | 673 | 3 | 2 | 509 | 0.80 |
| 9 | 1205 | 6 | 5 | 565 | 0.89 |
| 19 | 2511 | 12 | 9 | 1241 | 1.95 |
| 37 | 7760 | 39 | 19 | 2648 | 4.15 |
| 74 | 12057 | 60 | 38 | 1923 | 3.01 |
| 148 | 36991 | 184 | 75 | 2900 | 4.54 |

Example 2

Sensitivity Assay of Real-World Samples

In order to determine the limits of detection with practical samples, commercially available washing detergent was used by preparing a 10% solution in Ringer buffer as a test sample. Ten (10) mL of 10% sample and 10 mL of 10% sample spiked with a known amount of microorganism were each separately filtered through different 10 mL syringes fitted with a 0.45μ disc filter (filtration device) for the assay blank control and the assay sample, respectively, by applying positive pressure using the syringe plunger. The filters were washed with 20 mL of Ringer buffer. Three (3) mL of Letheen broth were added, 2 mL of which were filtered through the filtration device and 1 mL was separately retained, followed by immediate capping of the disc filter outlet tip with a fluid retention element to prevent leakage of liquids. The syringe device or filtration device was incubated upright at 32° C. for 6 hours, where the capped outlet was positioned below the capture filter that retains microorganisms, which is positioned below the vessel for receiving a sample or control. After incubation, the fluid retention element was removed, the broth was purged, and the plunger was removed from the vessel of the syringe. The outlet positioned below the filter disc was again capped and 300 μL of extractant and substrate ADP solution was added. The filtration device was incubated upright at room temperature for one hour. At the completion of the incubation period, the fluid retention element was removed and the contents were expelled into an assay cuvette. The cuvettes containing controls and samples were placed in a CELSIS ADVANCE™ Luminometer and injected with 100 μL of luciferase reagent to detect the amount of ATP produced by the adenylate kinase reaction. Detection of ATP indicated the presence of microbial contamination in the tested sample using adenylate kinase as a marker. In order to detect the sensitivity of the assay in Ringer buffer, various organisms grown in Letheen broth for 24 hours were diluted to have 100 CFU per mL followed by a two-fold dilution to theoretical 1 CFU or less cells per mL. The diluted cells were spiked into Ringer buffer to determine the limits of detection and signal to noise ratio. Corresponding unspiked sample was treated as a reagent blank. The cell counts were confirmed by plating on tryptone-soy agar plates. Triplicate values were generated and average values were expressed with standard error. The data of Table 2 depict the limits of detection together with signal to noise ratios for various organisms in consumer products. The asterisk (*) represents those values that are the average of three observations.

TABLE 2

| | B thuringiensis | | | B cepacia | |
|---|---|---|---|---|---|
| CELLS | MEAN RLU* | S/N RATIO* | CELLS | MEAN RLU* | S/N RATIO* |
| 0 | 190 | — | 0 | 273 | — |
| 0.53 | 76 | 0 | 1 | 313 | 1.15 |
| 1 | 6178 | 33 | 2 | 12428 | 45.52 |
| 2 | 64 | 0 | 4 | 714 | 2.62 |
| 4 | 138 | 1 | 9 | 761 | 2.79 |
| 9 | 845 | 4 | 17 | 2779 | 10.18 |
| 17 | 3626 | 19 | 34 | 5561 | 20.37 |
| 34 | 3519 | 19 | 69 | 13899 | 50.91 |
| 68 | 15088 | 79 | 137 | 26311 | 96.38 |

| | P. aeruginosa | |
|---|---|---|
| CELLS | MEAN RLU* | S/N RATIO* |
| 0 | 259 | — |
| 2.5 | 1043 | 4.03 |
| 5 | 1530 | 5.91 |
| 10 | 2311 | 8.92 |
| 20 | 9412 | 36.34 |
| 40 | 6557 | 25.32 |
| 80 | 19404 | 74.92 |
| 160 | 35975 | 138.90 |
| 320 | 138111 | 533.25 |

Example 3

Use of Pre-Filter and Capture Filter with Product Sample

A sample of a typical detergent product was found to rapidly clog the pores of conventional filters (typically 0.2μ-0.45μ in diameter) due to a high concentration of suspended particles within the sample. Less than 0.1 g sample was estimated to be the amount that could be passed through, making it effectively untestable by conventional filter-based methods. When examined, the particles within were found to range from about 1μ to about 50μ in diameter. To enable a suitable amount of sample to be filtered, the present novel system was developed consisting of two discrete filter elements, each designed to be used simultaneously.

The first filter, or 'pre-filter', contained two discs of woven nylon mesh filter, sealed within a syringe-filter housing. The pore-sizes of each disc were carefully selected such that the uppermost disc contained pores with a diameter of 20μ, and the lower disc contained pores with a diameter of 5μ. The diameter of the discs used in this example were 40 mm, but can be larger or smaller depending on the filterability challenge posed by the sample as an ordinarily skilled practitioner would understand. When the detergent sample was passed through the pre-filter alone, it was found that a sample amount of up to 10 g could be readily passed, with the pre-filter retaining all particles greater than 5μ. Additional experiments showed (Example 4) that microbial cells and spores were not retained to a significant extent by the pre-filter during this process.

The filter that retains microorganisms, or 'capture filter', contained a single disk of glass-fiber material, sealed within a syringe-filter housing, or filtration device. The glass-fiber material was manufactured such that it possessed a relative pore size of 0.7μ. The diameter of the disc used in this example was 30 mm, but a disc could be larger or smaller depending on the filterability challenge posed by the sample as an ordinarily skilled practitioner would understand. When the capture filter was attached to the outlet of the pre-filter, a sample amount of up to 1 g was readily passed through, yielding a ten-fold improvement in sample filterability when compared to conventional filter separation methods. In addition, this amount of filtered sample could still be washed by passing additional volumes of a suitable buffer through the filter—an important consideration when potentially inhibitory product traces need to be rinsed away. Additional experiments showed (Example 5) that the capture filter successfully retained most of the cells or spores that were passed through.

Example 4

Free Passage of Microbial Cells or Spores Through the Pre-Filter Component of the Filtration System An effective pre-filter must be shown to allow free passage of cells while sample is being passed through, because retained cells risk becoming lost to the final assay. Passage of bacterial cells and spores were checked for free passage through the pre-filter in two experiments:

Experiment 1—Passage of Bacterial Cells

A suspension containing low numbers of the Gram-negative bacterial species Burkholderia cepacia (ATCC 25416) was made in sterile phosphate buffer (Weber Scientific) and a 10% (w/v) suspension of detergent product containing particles requiring pre-filtration. The cell count was adjusted such that a 100 μL aliquot of the inoculated buffer or product suspension contained about 100 CFU. Duplicate counts of both suspensions were made on tryptone-soy agar by spreading 100 μL aliquots onto the agar surface, incubating at 30° C. for 48 hours and counting the colonies that grew. Counts were made at the start and end of the experiment to show that the bacterial count had not varied over time.

Volumes (10 ml) of both buffer and product cell suspensions were passed through a sterile 20μ mesh filter (identical to the upper mesh contained in the pre-filter), collected, and counted again as described above. The collected 20μ mesh filtrate was then passed through a sterile 5μ mesh filter (identical to the lower mesh contained in the pre-filter), collected, and counted again as described above. Results are shown in Table 3 as follows:

TABLE 3

| | B. cepacia PLATE COUNTS | | | |
|---|---|---|---|---|
| SAMPLE | START COUNT | POST 20μ MESH FILTER | POST 5μ MESH FILTER | END COUNT |
| CELLS IN BUFFER-ONLY | 115 | 149 | 120 | 156 |
| CELLS IN HIGH-PARTICULATE SAMPLE | 124 | 144 | 138 | 125 |

Counts indicated that no loss of cells occurred after passage through either mesh contained within the pre-filter, either in the buffer-only sample, or in the presence of sample particulates (high-particulate sample).

Experiment 2—Passage of Bacterial Spores

Suspensions containing low numbers of spores of the bacterial species Lysinibacillus sphaericus (ATCC 29726) and Bacillus thuringiensis subspecies kurstaki (strain SA-12) were made in sterile phosphate buffer (Weber Scientific) such that a 100 μL aliquot contained about 10-100 CFU. Duplicate counts of both suspensions were made on tryptone-soy agar by spreading 100 μL aliquots onto the agar surface, incubating at 30° C. for 48 hours, and counting the colonies that grew.

Volumes (10 mL and 50 mL) of both spore suspensions were passed through separate sterile pre-filters; the filtrates of which were collected and counted again in duplicate. Percentage pass-through values were calculated. Results are shown in Table 4 as follows:

TABLE 4

| | START COUNT | AFTER 10 mL FILTERED | AFTER 50 mL FILTERED |
|---|---|---|---|
| | *L. sphaericus* PLATE COUNTS (CFU) | | |
| COUNT 1 | 14 | 18 | 11 |
| COUNT 2 | 17 | 16 | 21 |
| AVERAGE | 15.5 | 17 | 16 |
| % PASS-THROUGH | — | 110% | 103% |
| | *B. thuringiensis* PLATE COUNTS (CFU) | | |
| COUNT 1 | 97 | 100 | 85 |
| COUNT 2 | 92 | 107 | 105 |
| AVERAGE | 94.5 | 103.5 | 95 |
| % PASS-THROUGH | — | 110% | 101% |

Results show that the pre-filter retained no spores, even after filtration of volumes up to 50 mL.

Example 5

Retention of Cells by the Capture Filter Component of the Filtration System

An effective capture filter must be shown to capture and retain a majority of cells that pass through it during filtration, so that they remain available for the final detection assay. Retention of bacterial cells and spores in the 0.7μ glass-fiber capture filter was checked in two experiments:

Experiment 1—Retention of Bacterial Cells

A suspension containing low numbers of the Gram-negative bacterial species *Burkholderia cepacia* (ATCC 25416) was made in sterile phosphate buffer (Weber Scientific) and a 10% (w/v) suspension of high-particulate detergent product that had been treated by prior passage through a sterile pre-filter. The cell count was adjusted such that a 100 μL aliquot of the inoculated buffer or product suspension contained about 100 CFU. Duplicate counts of both suspensions were made on tryptone-soy agar by spreading 100 μL aliquots onto the agar surface, incubating at 30° C. for 48 hours, and counting the colonies that grew.

Volumes (10 mL) of both cell suspensions were passed through sterile glass-fiber syringe filters with a variety of pore sizes: 3.1μ, 1.2μ, 1.0μ and 0.7μ. Filtrates were collected and counted again as described above. Results are shown in Table 5 as follows:

TABLE 5

|  | NO FILTRATION | 3.1μ FILTER | 1.2μ FILTER | 1.0μ FILTER | 0.7μ FILTER |
|---|---|---|---|---|---|
| *B. cepacia* PLATE COUNTS (CFU) - FILTERED IN BUFFER | | | | | |
| COUNT 1 | 166 | 95 | 70 | 35 | 0 |
| COUNT 2 | 197 | 97 | 59 | 28 | 0 |
| AVERAGE | 182 | 96 | 65 | 32 | 0 |
| *B. cepacia* PLATE COUNTS (CFU) - FILTERED IN SAMPLE | | | | | |
| COUNT 1 | 166 | 124 | 132 | 54 | 3 |
| COUNT 2 | 197 | 158 | 110 | 61 | 2 |
| AVERAGE | 182 | 141 | 121 | 58 | 3 |

Counts indicated that the 0.7μ glass-fiber filter retained virtually all cells passed through it making it suitable as a capture filter for high-particulate samples since the filtrate had few cells.

Experiment 2—Retention of Bacterial Spores

Suspensions containing low numbers of spores of the bacterial species *Lysinibacillus sphaericus* (ATCC 29726) and *Bacillus thuringiensis* subspecies *kurstaki* (strain SA-12) were made in sterile phosphate buffer (Weber Scientific) such that a 100 μL aliquot contained about 10-100 CFU. Duplicate counts of both suspensions were made on tryptone-soy agar by spreading 100 μL aliquots onto the agar surface, incubating at 30° C. for 48 hours, and counting the colonies that grew.

Volumes (50 mL) of both spore suspensions were passed through separate sterile pre-filters. The filtrates were collected and counted again in duplicate. Aliquots (10 mL) of each of the pre-filter filtrates were then passed through sterile 0.7μ glass-fiber capture filters. The capture filter filtrates were collected and counted again. Results are shown in Table 6 as follows:

TABLE 6

|  | START COUNT | POST PRE-FILTER | POST CAPTURE FILTER |
|---|---|---|---|
| *L. sphaericus* PLATE COUNTS (CFU) | | | |
| COUNT 1 | 14 | 11 | 0 |
| COUNT 2 | 17 | 21 | 0 |
| AVERAGE | 15.5 | 16 | 0 |
| *B. thuringiensis* PLATE COUNTS (CFU) | | | |
| COUNT 1 | 97 | 85 | 0 |
| COUNT 2 | 92 | 105 | 4 |
| AVERAGE | 94.5 | 95 | 2 |

Counts indicated that the 0.7μ glass-fiber capture filters retained virtually all spores passed through it making it suitable for use as a capture filter for high-particulate samples.

Example 6

Rapid Detection of Bacterial Cells and Spores in High-Particulate Product Using the Pre-Filter System The combined pre-filter and capture filter system was used to rapidly detect the presence of bacterial cells and spores in a large volume of high-particulate detergent product.

Experiment 1—Detection of Bacterial Cells

Low numbers of the Gram-negative bacterial species *Pseudomonas aeruginosa* (ATCC 9027) were inoculated into a 10% (w/v) suspension of high-particulate detergent product in buffer. Two inoculated suspensions were prepared in duplicate, such that 5 mL volumes contained about 5 cells and about 50 cells, respectively. Duplicate product suspensions containing no inoculated cells were prepared to serve as control samples. Duplicate counts of both inoculated suspensions were made on tryptone-soy agar by spreading 100 μL aliquots onto the agar surface, incubating at 30° C. for 48 hours, and counting the colonies that grew. Duplicate 5 mL volumes of all inoculated and non-inoculated product suspensions were passed through filtration devices each comprising a pre-filter and a capture filter that were connected in sequence. The connected filters were then washed by passing 10 mL sterile phosphate buffer (Weber Scientific) through each, after which the pre-filter was disconnected and discarded. The remaining capture filters from each filtration device were then loaded with nutrient broth and incubated for 6 hours at 30° C.

After incubation, the broth was expelled and discarded from each device comprising the capture filter. Each filtration device was then loaded with a mixture of 150 μL cell extractant reagent and 150 μL ADP substrate reagent. The reagent-filled devices were incubated at room temperature for 1 hour to allow any microbial adenylate kinase extracted from cells in the capture filters to react with and convert the ADP substrate to ATP.

After 1 hour, all filtration device contents were expelled and collected in separate measuring cuvettes to which 100 μL luciferase detection reagent was added. The luciferase detection reagent reacted with any generated ATP in the cuvettes to create light as measured in a luminometer, which produced a result value expressed in Relative Light/Luminescence Units (RLU). An average RLU from the inoculated samples greater than 2 times the average RLU from the non-inoculated control samples was considered sufficient to indicate the presence of microbial cells or a positive result. Results are shown in Table 7 as follows:

TABLE 7

| SAMPLE | AVERAGE RESULT (RLU) |
|---|---|
| PRODUCT CONTROL (0 CELLS) | 146 |
| PRODUCT + 4 CELLS | 17439 |
| PRODUCT + 36 CELLS | 55926 |

The results demonstrate the clear detection of low numbers of the species *Pseudomonas aeruginosa* in a high-particulate detergent sample after a brief 6 hour cell culturing or incubation period.

Experiment 2—Detection of Bacterial Spores

A commercial preparation of spores of the bacterial species *Bacillus thuringiensis* subspecies *kurstaki* (strain SA-12) was obtained. A suspension of spores in sterile phosphate buffer (Weber Scientific) was prepared from it and purified by pasteurization to eliminate any vegetative cells. Low numbers of spores from this were inoculated into buffer-only and into a 10% (w/v) suspension of high-particulate detergent product prepared in buffer. Two levels of inoculation were prepared in duplicate such that 10 mL volumes of each contained about 5 spores and about 50 spores, respectively. Duplicate buffer samples and product suspensions containing no inoculated spores were prepared to serve as control samples.

Duplicate counts of both inoculated suspensions were made on tryptone-soy agar by spreading 100 μL aliquots onto the agar surface, incubating at 30° C. for 72 hours, and counting the colonies that grew. Duplicate 10 mL volumes of all inoculated and non-inoculated product suspensions were passed through filtration devices each comprising a pre-filter and a capture filter that were connected in sequence. The connected filters were then washed by passing 20 mL sterile phosphate buffer (Weber Scientific) through each, after which the pre-filters were disconnected and discarded. The remaining capture filters from each filtration device were then loaded with nutrient broth and incubated for 6 hours at 30° C. to allow any captured spores to germinate.

After incubation, the broth was expelled and discarded from each device comprising the capture filter. Each filtration device was then loaded with a mixture of 150 μL cell extractant reagent and 150 μL ADP substrate reagent. The reagent-filled devices were incubated at room temperature for 1 hour to allow any microbial adenylate kinase extracted from germinated spores in the capture filters to react with and convert the ADP substrate to ATP.

After 1 hour, all filtration device contents were expelled and collected in separate measuring cuvettes to which 100 μL luciferase detection reagent was added. The luciferase detection reagent reacted with any generated ATP in the cuvettes to create light as measured in a luminometer, which produced a result value expressed in Relative Light Units (RLU). An RLU from the inoculated samples greater than 2 times the average RLU from the non-inoculated control samples was considered sufficient to indicate the presence of microbial cells or a positive result. Results are shown in Table 8 as follows:

TABLE 8

| SAMPLE | AVERAGE RESULT (RLU) |
|---|---|
| BUFFER CONTROL (0 SPORES) | 516 |
| BUFFER + 5 SPORES | 22574 |
| BUFFER + 54 SPORES | 418117 |
| PRODUCT CONTROL (0 SPORES) | 117 |
| PRODUCT + 5 SPORES | 16924 |
| PRODUCT + 54 SPORES | 47331 |

The results demonstrate the clear detection of low numbers of spores of the bacterial species *Bacillus thuringiensis* in a high-particulate detergent sample after a brief 6 hour cell culturing or incubation period.

Example 7

Rapid Detection of Bacterial Cells in Non-Filterable High-Particulate Product Using the Centrifugation System A non-filterable fabric softener naturally contaminated with cells similar to *B. cepacia* was examined in a comparison of growth media: Letheen broth and Peptone water, to determine which promotes more effective cell recovery and growth.

Undiluted sample contained bacteria in approximately $1\times10^{-6}$ to $1\times10^{-5}$ cfu. To provide a range of bacterial cells for the assay, the sample was serially diluted in ¼-strength Ringer buffer as follows (Table 9):

TABLE 9

| DILUTION NAME | SAMPLE AMOUNT (g) + | BUFFER AMOUNT (mL) = | DILUTION |
|---|---|---|---|
| A | 10 g sample | 90 mL buffer | $10^{-1}$ dilution (most concentrated) |
| B | 10 g $10^{-1}$ dilution | 90 mL buffer | $10^{-2}$ dilution |
| C | 10 g $10^{-2}$ dilution | 90 mL buffer | $10^{-3}$ dilution |
| D | 10 g $10^{-3}$ dilution | 90 mL buffer | $10^{-4}$ dilution |
| E | 10 g $10^{-4}$ dilution | 90 mL buffer | $10^{-5}$ dilution |
| CONTROL | 10 g Uncontaminated | 90 mL buffer | |

The $10^{-2}$ and $10^{-3}$ dilutions were also counted on Standard Methods agar (SMA, Becton-Dickinson) plates to obtain an estimate of the actual bacterial content of the sample. Plates were incubated at 30° C. for 72 hours prior to counting colonies.

The control sample and 10 mL of each dilution (Dilutions A-E) were added to 15 mL conical centrifuge tubes in duplicate. The tubes were centrifuged at 2000×g for 15 minutes to sediment the cells, at which point the supernatants were discarded. The pelleted cells were washed by resuspending them in 10 mL of fresh, sterile buffer, centrifuging again at 2000×g for 15 minutes, and discarding the supernatants. Letheen broth (Becton-Dickinson) was added to one set of tubes in an amount of 1 mL per tube, and 1 mL Peptone water (BBL) was added to each of the other duplicate tubes. All of the tubes were vortexed for 10 seconds at room temperature to fully resuspend the pelleted cells. All of the tubes were then incubated at 30° C. for 4 hours, shaking at 200 rpm. After incubation, all of the tubes were centrifuged at 2000×g for 15 minutes and the supernatants were discarded. Extractant reagent (Celsis LuminEX™) in an amount of 100 μl per tube and 100 μl of substrate reagent per tube (Celsis LuminAMP™) were then added to all tubes, which were vortexed for 10 seconds, then incubated at room temperature for 60 minutes to allow detectable signal to amplify. Each sample was transferred to a fresh cuvette and assayed for detection using a luminometer primed with bioluminescence reagent (Celsis LuminATE™). The luminometer automatically added 100 µL LuminATE™, then counted any emitted light for 1 second.

Results

The $10^{-2}$ sample plate-count produced an average count of 20 colonies. Based on this, the cell/sample estimates are as follows (Table 10):

TABLE 10

| | $10^{-5}$ DILUTION | $10^{-4}$ DILUTION | $10^{-3}$ DILUTION | $10^{-2}$ DILUTION | $10^{-1}$ DILUTION |
|---|---|---|---|---|---|
| CELL/TEST ESTIMATE | 2 | 20 | 200 | 2000 | 20000 |

Table 11 and Table 12 show the results of the relative light units for the controls and samples, respectively:

TABLE 11

| | TUBE 1 | TUBE 2 | AVG RLU |
|---|---|---|---|
| BROTH (NO INCUBATION) | | | |
| LETHEEN-ONLY | 24 | 16 | 20 |
| PEPTONE-ONLY | 12 | 10 | 11 |
| UNSPOILT FABRIC SOFTENER | | | |
| LETHEEN INCUBATION | 532 | 500 | 516 |
| PEPTONE INCUBATION | 250 | 332 | 291 |

TABLE 12

| | TUBE 1 | TUBE 2 | AVG RLU | SD | CV % |
|---|---|---|---|---|---|
| LETHEEN INCUBATION | | | | | |
| $10^{-5}$ DILUTION | 1177 | 386 | 782 | 396 | 51 |
| $10^{-4}$ DILUTION | 1703 | 667 | 1185 | 518 | 44 |
| $10^{-3}$ DILUTION | 4330 | 3148 | 3739 | 591 | 16 |
| $10^{-2}$ DILUTION | 50096 | 99443 | 74770 | 24674 | 33 |
| $10^{-1}$ DILUTION | 698206 | 498780 | 598493 | 99713 | 17 |
| PEPTONE INCUBATION | | | | | |
| $10^{-5}$ DILUTION | 1310 | 787 | 1049 | 262 | 25 |
| $10^{-4}$ DILUTION | 1616 | 753 | 1185 | 432 | 36 |
| $10^{-3}$ DILUTION | 10326 | 9843 | 10085 | 242 | 2 |
| $10^{-2}$ DILUTION | 127304 | 78799 | 103052 | 24253 | 24 |
| $10^{-1}$ DILUTION | 181526 | 551809 | 366668 | 185142 | 50 |

The presence of as few as two captured microbial cells are clearly revealed by the assay results from the spoilt-product dilutions.

Example 8

Rapid Detection of Bacterial Cells in Buffer Using Centrifugation And Bead Sedimentation Cells of the bacterial species *Gluconacetobacter liquifaciens* (ATCC 14835) were prepared in sterile buffer (Weber Scientific) such that approximately 100 and 1000 cells could be inoculated into samples. Aliquots of 10 mL sterile buffer (Weber Scientific) were dispensed into sterile 15 mL conical centrifuge tubes (CellTreat®), which were split into two sets. To one set, 100 µL of 0.76µ polystyrene microsphere beads (5% solids (w/v), Bangs Laboratories, Inc.™) were added, while the other set of tubes received no beads. Duplicate tubes in each set were inoculated with either 100 or 1000 cells of *G. liquifaciens*, with duplicate control tubes receiving no cells. All tubes were then centrifuged at 2000×g for 15 minutes and the supernatants were discarded from each. Letheen broth (Becton-Dickinson) in an amount of 3 mL was then added to all tubes, which were vortexed for 10 seconds to resuspend pelleted cells and beads (if present). All tubes were then incubated statically at 31° C. for 5 hours. Following incubation, all tubes were centrifuged at 2000×g for 15 minutes at room temperature, and the broth supernatants were discarded. Extractant reagent (Celsis LuminEX™) in an amount of 100 µl per tube and 100 µl per tube of substrate reagent (Celsis LuminAMP™) were then added to all tubes, followed by vortexing for 10 seconds, and then incubation at room temperature for 60 minutes to allow detectable signal to amplify. Each sample was transferred to a fresh cuvette and assayed for detection using a luminometer primed with bioluminescence reagent (Celsis LuminATE™). The luminometer automatically added 100 µL LuminATE™ detection assay reagent, then counted any emitted light for 1 second.

Results

Cell counts (aim and actual) are presented in Table 13:

TABLE 13

| CELL INOCULA (CFU/100 µL) | |
|---|---|
| AIM | ACTUAL |
| 100 | 38 |
| 1000 | 380 |

The luminometer produced results expressed as relative light units (RLU). The RLU from control and test samples with and without added beads are presented in Table 14:

TABLE 14

| SAMPLE | TUBE 1 | TUBE 2 | AVERAGE |
|---|---|---|---|
| 0 CELL CONTROL | 324 | 259 | 292 |
| 38 CELLS (−) BEADS | 445 | 495 | 470 |
| 380 CELLS (−) BEADS | 2276 | 1242 | 1759 |
| 38 CELLS (+) BEADS | 1803 | 1389 | 1596 |
| 380 CELLS (+)BEADS | 15159 | 36890 | 26025 |

The presence of beads clearly produced higher RLU, with as few as 38 cells producing an average RLU result greater than twice the control RLU average.

While various embodiments have been described above, it should be understood that such disclosures have been presented by way of example only and are not limiting. Thus, the breadth and scope of the subject methods, devices, and systems should not be limited by any of the above-described exemplary embodiments, but should be defined only in accordance with the following claims and their equivalents.

Having now fully described the subject methods, devices, and systems, it will be understood by those of ordinary skill in the art that the same can be performed within a wide and equivalent range of conditions, formulations and other parameters without affecting their scope or any embodiment thereof. All cited patents, patent applications and publications are fully incorporated by reference in their entirety.

We claim:

1. A method of detecting microorganisms in a sample potentially containing microorganisms, comprising:
   a) filtering the sample through a pre-filter for allowing microorganisms to flow through;
   b) filtering the pre-filter filtrate through a capture filter for retaining microorganisms;
   c) culturing the microorganisms retained on the capture filter;
   d) lysing the cultured microorganisms with extractant in combination with adenosine diphosphate;
   e) filtering the lysed microorganisms through the capture filter;
   f) adding luciferin and luciferase to the lysed microorganism filtrate, which produces a light; and
   g) detecting the light using a luminometer, which indicates the presence of microorganisms in the sample.

2. The method of claim 1, wherein the pre-filter is a filter of a double-layer filter or two separate filters.

3. A method of detecting microorganisms in a sample containing microorganisms, comprising:
   a) filtering the sample through a pre-filter for allowing microorganisms to flow through;
   b) filtering the pre-filter filtrate through a capture filter for retaining microorganisms;
   c) culturing the microorganisms retained on the capture filter;
   d) lysing the cultured microorganisms with extractant in combination with a marker molecule substrate;
   e) filtering the lysed microorganisms through the capture filter;
   f) adding a detection assay reagent to the lysed microorganism filtrate, which produces a light; and
   g) detecting the light using a detection device, which indicates the presence of microorganisms in the sample.

4. The method of claim 2, wherein the double-layer filter and two separate filters each has filters of sequentially decreasing pore sizes.

5. The method of claim 1, wherein the sample contacts the pre-filter comprising a first filter having a pore size large enough to allow passage of microorganisms and retain non-microbial particles and a second filter having a pore size that is smaller than that of the first filter and large enough to allow passage of microorganisms and retain non-microbial particles.

6. The method of claim 2, wherein the first and second filters of the pre-filter have a pore size ranging from about 5 to about 100 microns.

7. The method of claim 1, wherein the capture filter has a pore size ranging from about 0.2 to about 4 microns.

* * * * *